United States Patent [19]

Mayer et al.

[11] Patent Number: 5,840,995
[45] Date of Patent: Nov. 24, 1998

[54] PRECURSOR FOR ALKOXYLATION CATALYSTS

[75] Inventors: Michael Mayer, Goldbach; Joachim Hess, Hofheim; Alfred Babiel, Villmar, all of Germany

[73] Assignee: Hoechst Aktiengesellschaft, Frankfurt, Germany

[21] Appl. No.: 763,715

[22] Filed: Dec. 13, 1996

[30] Foreign Application Priority Data

Dec. 15, 1995 [DE] Germany .................. 195 46 946.1

[51] Int. Cl.⁶ ............................................. C07C 41/03
[52] U.S. Cl. ......................... 568/618; 568/678; 564/475
[58] Field of Search ................... 568/618, 678; 564/475

[56] References Cited

U.S. PATENT DOCUMENTS 4,894,485  1/1990  Behler et al. .
4,996,364  2/1991  Behler et al. .
5,600,020  2/1997  Wehle et al. .

FOREIGN PATENT DOCUMENTS 0 092 256  10/1983  European Pat. Off. .
0 295 578  12/1988  European Pat. Off. .
0 337 239  10/1989  European Pat. Off. .
43 41 576   6/1995  Germany .

*Primary Examiner*—Gary Geist
*Assistant Examiner*—Sreeni Padmanabhan
*Attorney, Agent, or Firm*—Scott E. Hanf

[57] ABSTRACT

A precursor for alkoxylation catalysts is prepared by reacting a chelating anionic or nonionic phase transfer catalyst with an alkaline earth metal compound in the presence of a compound which can be alkoxylated. Suitable phase transfer catalysts are, in particular, ethoxylated fatty alcohols, ether carboxylic acids, ether sulfonic acids or ether phosphonic acids. Addition of sulfuric acid to such a precursor produces an alkaline earth metal sulfato complex which is the actual catalyst for the alkoxylation.

10 Claims, No Drawings

PRECURSOR FOR ALKOXYLATION CATALYSTS

The conventional alkoxylation, for example of fatty alcohols and amines, gives alkoxylates having a broad molecular weight distribution. A narrower molecular weight distribution can be achieved if narrow range catalysts are employed. These give a reduction in the proportions of unalkoxylated starting material and a reduction in the proportion of highly alkoxylated products. Narrow range catalysts which have already been described are alkaline earth metal salts of organic carboxylic acids (U.S. Pat. No. 4,282,387; EP 85 107), alkaline earth metal salts of ether carboxylic acids (EP 295 578) and alkaline earth metal salts of vicinal hydroxy, alkoxy-substituted fatty acids (DE 3 706 047). It is common to all these catalysts that the alkaline earth metal salts are defined salts which are prepared separately and are added in this form to the alkoxylation reaction. In addition, the use of calcium sulfate as a narrow range catalyst is also known (EP-A-0301 621).

It has now been found that another suitable narrow range catalyst is an alkaline earth metal sulfato complex which is generated immediately prior to the alkoxylation reaction from a precursor containing an alkaline earth metal compound by addition of sulfuric acid.

The invention provides a precursor for alkoxylation catalysts, where this precursor is prepared by reacting a chelating anionic or nonionic phase transfer catalyst with an alkaline earth metal compound in the presence of a compound which can be alkoxylated. Suitable chelating anionic or nonionic phase transfer catalysts are, in particular, compounds of the formula 1

$$C_8\text{–}C_{22}\text{-alkyl}\text{—}O(AO)_x\text{—}B \qquad (1),$$

where

A is —$C_2H_4$— or —$C_3H_7$—,

B is hydrogen or a group of the formulae —$CH_2COOH$, —$SO_3H$ or —$PO(OH)_2$ and X is from 2 to 10.

The compound used in this reaction as the compound which can be alkoxylated is advantageously the same compound which is subsequently to be alkoxylated with the aid of this precursor or the catalyst prepared therefrom. Such compounds are in principle all compounds containing active hydrogen, for example monoalcohols, polyalcohols (glycols) or alkylphenols. Preference is given to saturated or unsaturated fatty alcohols, preferably having from 8 to 18 carbon atoms or their mixtures such as tallow fatty alcohol, lauryl alcohol, stearyl alcohol or oxoalcohols. As alkalkine earth metal compound, preference is given to calcium compounds such as calcium oxide, calcium hydroxide, calcium carbonate, calcium chloride, calcium acetate or other calcium salts. The compounds of the formula (1) are alkoxylated fatty alcohols (B=H) or the ether carboxylic acids, ether sulfonic acids or ether phosphonic acids derived therefrom.

The individual components for the precursor are generally used in the following molar ratios: from 0.1 to 3 mol, preferably from 0.1 to 0.5 mol, of the compound which can be alkoxylated together with from 0.4 to 2.5 mol, preferably from 0.4 to 1 mol, of a compound of the formula (1) having B=hydrogen or from 2 to 2.5 mol, preferably 2.2 mol, of the compound which can be alkoxylated together with from 1.5 to 1.95 mol, preferably from 1.7 to 1.8 mol, of an ether carboxylic acid, ether sulfonic acid or ether phosphonic acid as the compound of the formula (1). These figures for the molar amounts are in each case based on 1 mol of the alkaline earth metal cations.

In the preparation of the precursor, the alkaline earth metal compound is reacted with the compound of the formula (1). This is achieved by stirring a mixture of these two components at room temperature together with the compound which can be alkoxylated. If the compound of the formula (1) has B=hydrogen, this gives the corresponding alkoxide. In other cases, the alkaline earth metal salt of the ether carboxylic acid, ether sulfonic acid or ether phosphonic acid is formed. Relatively short reaction times of the order of 30 minutes are sufficient for forming these salts. In contrast, for the formation of the alkoxides it has been found to be advantageous to carry out the reaction over a longer period of time (up to 5 hours) and at higher temperatures (from about 100° to 120° C.). Water-soluble calcium salts such as calcium acetate or calcium chloride are used in the form of an aqueous solution, insoluble or sparingly soluble calcium compounds such as calcium carbonate or calcium hydroxide are added as solids. In the case of calcium oxide, it is advantageous to add a small amount of water in order to convert the calcium oxide at least partially into calcium hydroxide. After the reaction is complete, the water present is removed by distillation, preferably with the aid of an entrainer such as xylene or toluene. After removing the water, the remaining entrainer is likewise removed by distillation. In general, the entrainer, for example xylene, is added to the reaction mixture before the commencement of the reaction. If only small amounts of water are present after the preparation of the precursor, this water can remain in the precursor. It is then removed after the preparation of the actual catalyst and before the alkoxylation reaction. To remove any residual solids, it is advisable to filter the finished precursor.

The precursor prepared in this way is a homogeneous solution which has very good stability on storage. The actual alkoxylation catalyst in the form of an alkaline earth metal sulfato complex is produced from this precursor by addition of sulfuric acid immediately prior to the alkoxylation. Only this addition of sulfuric acid generates the functional catalyst. The amount of sulfuric acid is such that the molar ratio of sulfate ions to alkaline earth metal cations does not exceed 0.8:1. To complete this reaction, the mixture is generally stirred for from about 0.5 to 1 hour at from 80° to 100° C. Subsequently, the water present is removed by distillation by heating at from about 50° to 100° C. under reduced pressure. The actual alkoxylation reaction is then carried out by metering in ethylene oxide, propylene oxide or a mixture thereof in accordance with the methods customary for this purpose, with the compound which is to be alkoxylated, for example a $C_8$–$C_{18}$-fatty alcohol, being mixed with the precursor before adding the sulfuric acid.

As an alternative to the process described above, it is also possible to omit isolation of the precursor and generate the precursor directly in the reactor for the alkoxylation. For this purpose, the total amount of compound to be alkoxylated is initially charged and mixed by stirring with an alkaline earth metal compound or an aqueous solution of an alkaline earth metal salt plus a compound of the formula (1) using a method similar to the abovedescribed process for preparing the precursor. The alkaline earth metal sulfato complex is subsequently formed by addition of the sulfuric acid. This gives a stable oil-in-water emulsion, with the compound of the formula (1) also serving as emulsion stabilizer. The catalytic activity of the alkaline earth metal sulfato complex is determined by the ratio of water to compound of the formula (1). After formation of the alkaline earth metal sulfato complex, the water is removed by distillation and the alkoxylation is carried out by customary methods.

The precursor according to the invention or the catalyst in the form of the alkaline earth metal sulfato complex prepared therefrom has a high catalytic activity. This results in the time required for the alkoxylation being significantly shortened. In addition, the alkoxylates have a very narrow homologue distribution.

EXAMPLE 1

Amounts Used 0.5 mol of ether carboxylic acid of the formula $C_{12}H_{25}O-(C_2H_4O)_{3-6}-CH_2-COOH$ 3 mol of xylene 0.6 mol of $C_{12}$-fatty alcohol 0.27 mol of calcium hydroxide 1% by weight of Celite®J4 (filter aid based on silicate)

The calcium hydroxide is stirred into the mixture of ether carboxylic acid, xylene and fatty alcohol. After stirring for half an hour, the water is distilled off at from 100° to 120° C. and the remaining xylene is then distilled off at 160° C. 1% by weight, based on the total mixture, of Celite J4 is added and the mixture is filtered at 90° C. through a paper filter to give a clear solution.

24 g of the resulting precursor having a calcium content of 2.88% are mixed with 630 g of $C_{12}$-fatty alcohol. 3.2 ml of 1 molar sulfuric acid are then added and the mixture is stirred further for half an hour at 80° C. The water is then taken off at 100° C. under reduced pressure. The ethoxylation is then carried out at from 150° to 160° C. by adding the desired amount of ethylene oxide (2, 5 or 10 mol of ethylene oxide).

EXAMPLE 2

Amounts Used 0.5 mol of ethoxylated fatty alcohol of the formula $C_{12}H_{25}O-(C_2H_4O)_5H$ 3 mol of xylene 0.6 mol of fatty alcohol of the formula $C_{12}H_{25}OH$ 0.27 mol of calcium hydroxide 1% by weight of Celite J4

Ethoxylated fatty alcohol, xylene and fatty alcohol are stirred together and the calcium hydroxide is then added while stirring. After stirring for 30 minutes at room temperature, the water is removed by distillation under reduced pressure at from 100° to 120° C. Residual xylene is distilled off under reduced pressure at 160° C. 1% by weight of Celite J4 is added and the mixture is filtered at 90° C. through a paper filter to give a clear solution.

EXAMPLE 3

Amounts Used 0.5 mol of ethoxylated fatty alcohol of the formula $C_{12}H_{25}O-(C_2H_4O)_5H$ 0.5 mol of fatty alcohol of the formula $C_{12}H_{25}OH$ 1.25 mol of calcium oxide 1% by weight of water 1% by weight of Celite J4

The calcium oxide and then 1% by weight of water, based on the total mixture, are stirred into the mixture of ethoxylated fatty alcohol and fatty alcohol. After stirring for 2 hours at from 100° to 120° C., 1% by weight, based on the total mixture, of Celite J4 is added and the mixture is filtered at 90° C. through a paper filter to give a clear solution.

EXAMPLE 4

10.6 g of an aqueous solution of calcium acetate (10 g of water and 0.6 g of calcium acetate) are stirred into 600 g of a $C_{12}$–$C_{16}$-fatty alcohol. To this mixture are added 1.8 g of a $C_{12}$–$C_{16}$-fatty alcohol ethoxylated with 2 mol of ethylene oxide and the resulting emulsion is stirred for 2 hours at from 50° to 70° C. It is then dried under reduced pressure at 100° C., 2 ml of 1 molar sulfuric acid are added, the mixture is stirred for 1 hour and finally the water is distilled off.

The ethoxylation subsequent to the preparation of precursor and catalyst described in Examples 2 to 4 is carried out as described in Example 1.

We claim:

1. An alkoxylation catalyst comprising a mixture of an active hydrogen containing compound and a reaction product of the components comprising:

(a) a compound of the formula $C_8$–$C_{22}$-alkyl—$O(AO)_x$—B where

A is —$C_2H_4$— or —$C_3H_6$—,

B is hydrogen or a group of the formula —$CH_2COOH$, —$SO_3H$, or —$PO(OH)_2$ and x is from 2 to 10;

(b) an alkaline earth metal compound; and (c) sulfuric acid.

2. An alkoxylation catalyst as claimed in claim 1, wherein said alkaline earth metal compound is a calcium compound, and said active hydrogen-containing compound is selected from the group consisting of monoalcohol, polyalcohol or alkylphenol.

3. An alkoxylation catalyst as claimed in claim 1, wherein said alkaline earth metal compound is calcium oxide, calcium hydroxide or a calcium salt.

4. An alkoxylation catalyst as claimed in claim 1, wherein said calcium compound has been combined with said compound of the formula $C_8$–$C_{22}$-alkyl—$O(AO)_x$—B and said active hydrogen-containing compound while dissolved in an aqueous solution.

5. An alkoxylation catalyst as claimed in claim 1, wherein said active hydrogen-containing compound comprises at least one fatty alcohol.

6. An alkoxylation catalyst as claimed in claim 1, wherein said active hydrogen-containing compound comprises at least one fatty alcohol having 8 to 18 carbon atoms.

7. A process for alkoxylating an active hydrogen-containing compound, comprising:

adding an alkyene oxide to an active hydrogen-containing compound in the presence of the alkoxylation catalyst of claim 1.

8. A process as claimed in claim 7, wherein said active hydrogen-containing compound comprises at least one fatty alcohol.

9. A process for alkoxylating an active hydrogen-containing compound, comprising:

introducing a first portion of an active hydrogen containing compound into a reaction zone together with a compound of the formula $C_8$—$C_{22}$-alkyl—$O(AO)_x$—B, wherein A, B and x are as defined in claim 1 and an alkaline earth metal compound;

reacting said compound of the formula $C_8$–$C_{22}$-alkyl—$O(AO)_x$—B with said alkaline earth metal compound to obtain an alkoxylation catalyst precursor;

adding the second portion of said active hydrogen containing compound;

reacting said alkoxylation catalyst precursor with sulfuric acid; and alkoxylating all active hydrogen containing compound with an alkylene oxide.

10. A process for alkoxylating an active hydrogen-containing compound, comprising:

introducing the total amount of an active hydrogen containing compound into a reaction zone together with a compound of the formula $C_8$–$C_{22}$-alkyl—O(AO)$_x$—B, wherein A, B and x are as defined in claim 1 and an alkaline earth metal compound;

reacting said compound of the formula $C_8$–$C_{22}$-alkyl—O(AO)$_x$—B with said alkaline earth metal compound to obtain an alkoxylation catalyst precursor;

reacting said alkoxylation catalyst precursor with sulfuric acid; and alkoxylating all active hydrogen containing compound with an alkylene oxide.

* * * * *